US008775093B2

(12) United States Patent
Anderson et al.

(10) Patent No.: US 8,775,093 B2
(45) Date of Patent: Jul. 8, 2014

(54) PATTERN RECOGNITION SYSTEM FOR CLASSIFYING THE FUNCTIONAL STATUS OF PATIENTS WITH PULMONARY HYPERTENSION, INCLUDING PULMONARY ARTERIAL AND PULMONARY VASCULAR HYPERTENSION

(75) Inventors: Stephen T. Anderson, North Oaks, MN (US); Dean J. MacCarter, Engelwood, CO (US)

(73) Assignee: Shape Medical Systems, Inc., St. Paul, MN (US)

( * ) Notice: Subject to any disclaimer, the term of this patent is extended or adjusted under 35 U.S.C. 154(b) by 984 days.

(21) Appl. No.: 12/567,005

(22) Filed: Sep. 25, 2009

(65) Prior Publication Data

US 2010/0016750 A1 Jan. 21, 2010

Related U.S. Application Data

(63) Continuation-in-part of application No. 12/209,376, filed on Sep. 12, 2008, now abandoned.

(60) Provisional application No. 60/993,998, filed on Sep. 17, 2007.

(51) Int. Cl.
*G06F 19/00* (2011.01)
*A61B 5/083* (2006.01)
*A61B 5/091* (2006.01)
*A61B 5/0205* (2006.01)
*A61B 5/00* (2006.01)

(52) U.S. Cl.
CPC .......... *G06F 19/3431* (2013.01); *A61B 5/0205* (2013.01); *A61B 5/0836* (2013.01); *A61B 5/7264* (2013.01); *A61B 5/7275* (2013.01)
USPC .............................. 702/19; 600/532; 600/538

(58) Field of Classification Search
CPC .. A61B 5/0833; A61B 5/0836; A61B 5/7264; A61B 5/7275; A61B 5/4884; A61B 5/02028; A61B 5/0205; G06F 19/3487; G06F 19/345
See application file for complete search history.

(56) References Cited

U.S. PATENT DOCUMENTS

| 4,930,519 A | 6/1990 | Anderson et al. |
| 2003/0208106 A1 | 11/2003 | Anderson et al. |
| 2004/0138716 A1 | 7/2004 | Kon et al. |
| 2004/0260185 A1 | 12/2004 | Anderson et al. |

OTHER PUBLICATIONS

Hansen et al. Mixed-Expired and End-Tidal CO2 Distinguish Between Ventilation and Perfusion Defects During Exercise Testing in Patients Wigh Lung and Heqart Diseases. Chest vol. 132, pp. 977-983 (2007).*

Yeo et al. Value of a Doppler-Derived Combining Systolic and Diastolic Time Intervals in Predicting Outcome in Primary Pulmonary Hypertension. American Journal of Cardiology vol. 81, pp. 1157-1161 (1998).*

Wensel et al. Assessment of Survival in Patients With Primary Pulmonary Hypertension. Circulation vol. 106, pp. 319-324 (2002).*

SigmaPlot 8.0 Users Guide pp. 1-526 SPSS Inc. Chicago (2002).*

Fletcher et al. Medical/Scientific Statements: Special Report: Exercise Standards: A Statement for Healthcare Professionals From the American Heart Association. Circulation vol. 9, pp. 580-615 (1995).*

Miyamoto et al. Clinical Correlates and Prognostic Significance of Six-minute Walk Test in Patients with Preimary Pulmonary Hypertension American Journal of Respiratory and Critical Care Medicine vol. 161, pp. 487-492 (2000).*

Aaronson et al. Development and Perspective Validation of a Clinical Index to Predict Survival in Ambulatory Patients Referred for Cardiac Transplant Evaluation Circulation vol. 95, pp. 2662-2667 (1997).*

Dresing et al, American Journal of Cardiology, *Usefulness of Impaired Chronotropic Response to Exercise as a Predictor of Mortality, Independent of the severity of Coronary Artery Disease*, vol. 86, Sep. 15, 2000, pp. 602-609.

Robbins et al, Circulation—Journal of the American Heart Asssociation, *Ventilatory and Heart Rate Response to Exercise: Better Predictors of Heart Failure Mortality Than Peak Oxygen Consumption*, vol. 100, 1999, pp. 2411-2417.

Vivekananthan et al, Journal of the American College of Cardiology, *Heart Rate Recovery After Exercise is a Predictor of Mortality, Independent of the Angiographic Severity of Coronary Disease*, vol. 42, No. 5, 2003, pp. 831-838.

Watanabe et al, Circulation—Journal of the American Heart Asssociation, *Heart Rate Recovery Immediately After Treadmill Exercise and Left Ventricular Systolic Dysfunction as Predictors of Mortality: The Case of stress Echocardiography*, vol. 104, 2001, pp. 1911-1916.

(Continued)

*Primary Examiner* — John S Brusca
(74) *Attorney, Agent, or Firm* — C. G. Mersereau; Nikolai & Mersereau, P.A.

(57) ABSTRACT

A method employing pattern recognition techniques for identifying the functional status of patients with Pulmonary Hypertension is described. This method describes a process by which sets of cardiopulmonary exercise gas exchange variables are measured during rest, exercise and recovery and stored as unique data sets. The data sets are then analyzed by a series of feature extraction steps, yielding a multi-parametric index ($MPI_{PH}$) which reflects the current functional status of a patient. The method also employs a description scheme that provides a graphical image that juxtaposes the measured value of MPI to a reference classification system. An additional description scheme provides a trend plot of MPI values measured on a patient over time to provide feedback to the physician on the efficacy of therapy provided to the patient. The method will enable physicians to gather, view, and track complicated data using well-understood visualization techniques to better understand the consequences of their therapeutic actions.

15 Claims, 10 Drawing Sheets

(56) References Cited

OTHER PUBLICATIONS

Arena et al, Journal of Cardiac Failure, *The Minute Ventilation/Carbon Dioxide Production Slope is Prognostically Superior to the Oxygen Uptake Efficiency Slope*, vol. 13, No. 6, 2007, pp. 462-469.

Davies et al, European Heart Journal, *Enhanced Prognostic Value From Cardiopulmonary Exercise Testing in Chronic Heart Failure by Non-Linear Analysis: Oxygen Uptake Efficiency Slope*, vol. 27, 2006, pp. 684-690.

Hollenberg et al, Journal of American College of Cardiology, *Oxygen Uptake Efficiency Slope: An Index of Exercise Performance and Cardiopulmonary Reserve Requiring Only Submaximal Exercise*, vol. 36, No. 1, 2000, pp. 194-201.

Arena et al, Chest Journal, *Influence of Heart Failure Etiology on the Prognostic Value of Peak Oxygen Consumption and Minute Ventilation/Carbon Dioxide Production Slope*, vol. 128, 2005, pp. 2812-2817.

Corra et al, American Heart Journal, *Ventilatory Response to Exercise Improves Risk Stratification in Patients with Chronic Heart Failure and Intermediate Functional Capacity*, vol. 143, 2002, pp. 418-426.

Guazzi et al, American Heart Journal, *Exercise Oscillatory Breathing and Increased Ventilation to Carbon Dioxide Production Slope in Heart Failure: An Unfavorable Combination with High Prognostic Value*, vol. 153, 2007, pp. 859-867.

Kleber et al, Circulation—Journal of the American Heart Asssociation, *Impairment of Ventilatory Efficiency in Heart Failure: Prognostic Impact*, vol. 101, 2000, pp. 2803-2809.

Ponikowski et al, Circulation—Journal of the American Heart Asssociation, *Enhanced Ventilatory Response to Exercise in Patients With Chronic Heart Failure and Preserved Exercise Tolerance: Marker of Abnormal Cardiorespiratory Reflex Control and Predictor of Poor Prognosis*, vol. 103, 2001, pp. 967-972.

Arena et al, Circulation—Journal of the American Heart Asssociation,, *Development of a Ventilatory Classification System in Patients with Heart Failure*, vol. 115, 2007, pp. 2410-2417.

McRae III et al, Journal of American College Cardiology, *The Oxygen Uptake Efficiency Slope as a Predictor of Mortality in Chronic Heart Failure*, vol. 43, 2002, pp. 856-863.

\* cited by examiner

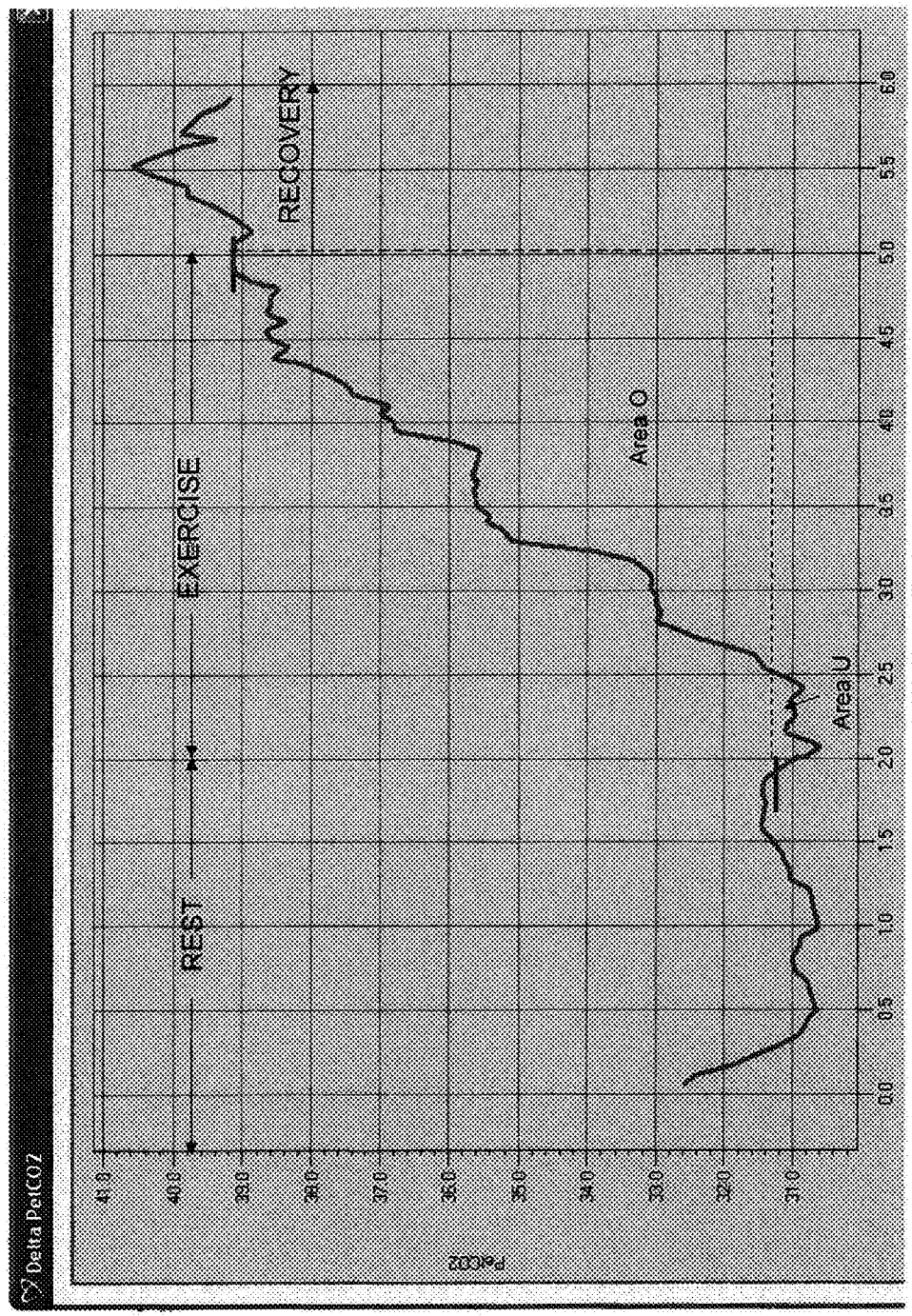
Figure 4 – Normal response to Exercise

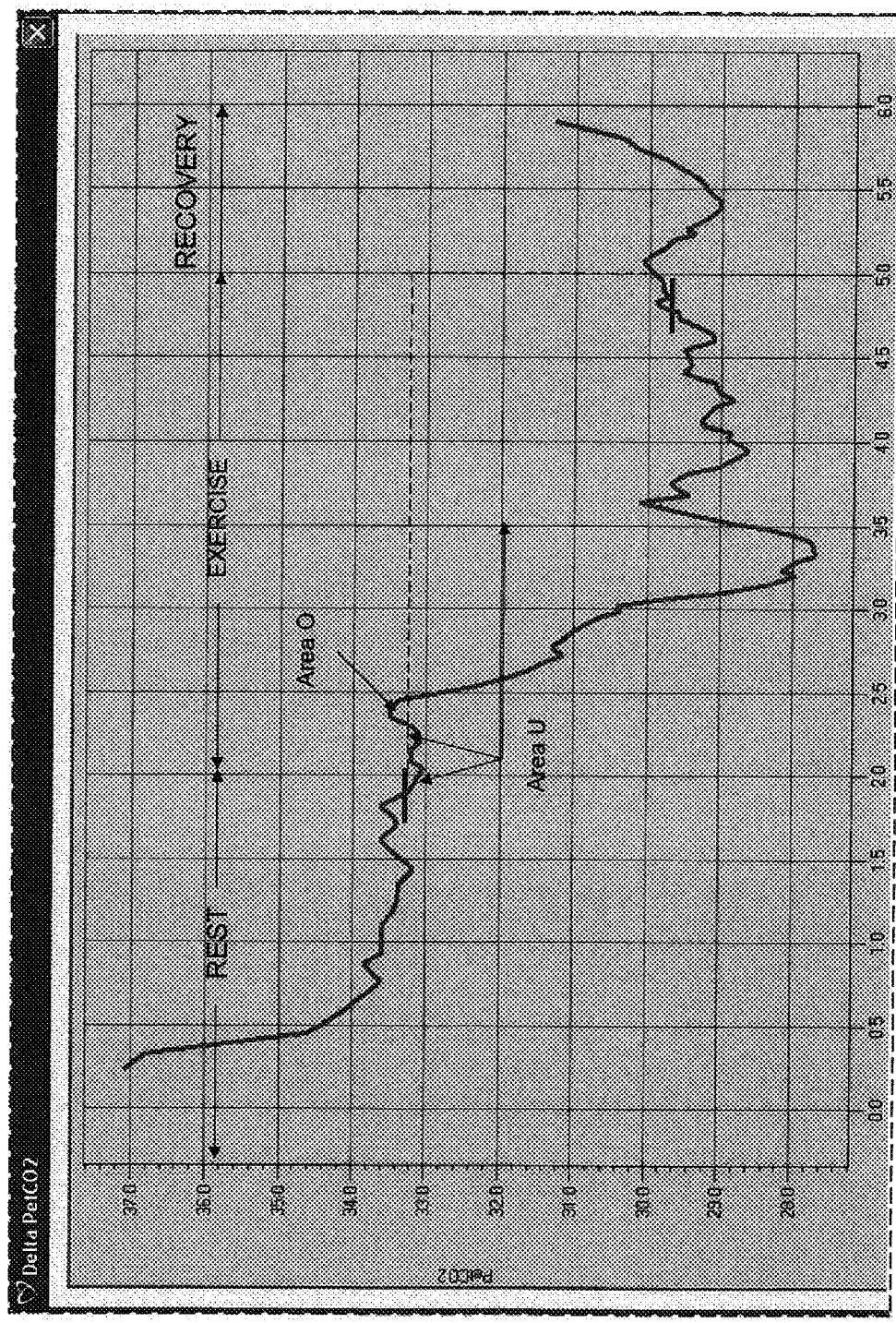
Fig. 5 - ETCO2 vs. time

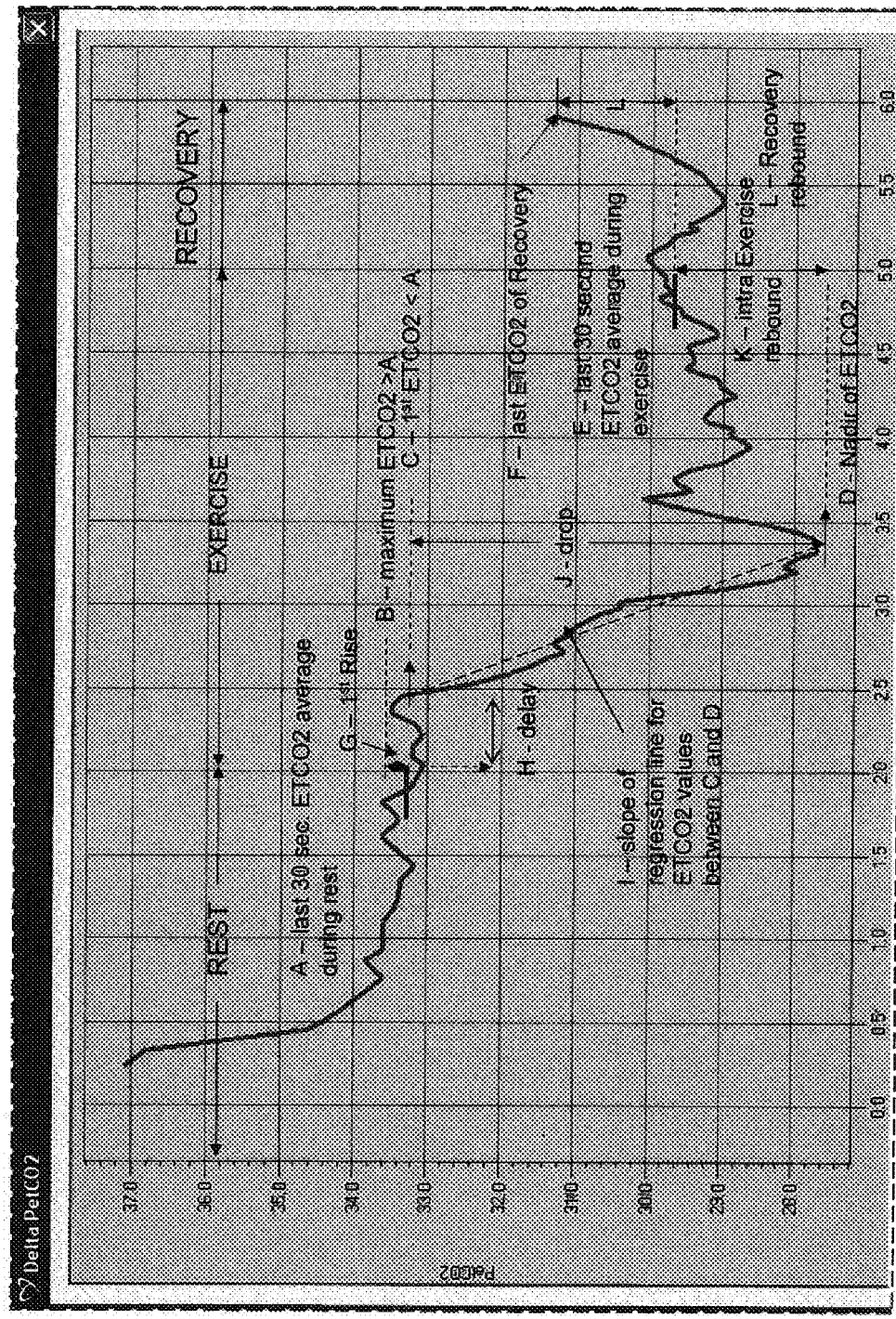
Fig. 6 - ETCO2 vs. time

Fig. 7 - Analysis Flowchart

If E-A > 1.8 and Area O/Area U > 1, Exit
Compute $MPI_{PH}$ according to the following formula:

$MPI_{PH} = (A-35mmHg) + G*W1 + H*W2 + I*W3 + J*W4 + K*W5 + L*W6$

For the example in Fig. 5,
A=33.4 mmHg
B=33.6 mmHg
C=33.35 mmHg
D=27.6 mmHg
E=29.6 mmHg
F=31.4 mmHg
G= B-A =.2 mmHg
H= .45 seconds
I= -6.25
J= D-C = -5.75 mmHg
K= E-D = 2.0 mmHg
L= E-F = -1.8 mmHg Assuming W1,W2,W3,W4,W5,W6 = 1.0
$MPI_{PH}$ = -1.9+.4+.45-6.25-5.75+2.0-1.8 = -11.15

Sign (negative) and magnitude indicate severity of PH

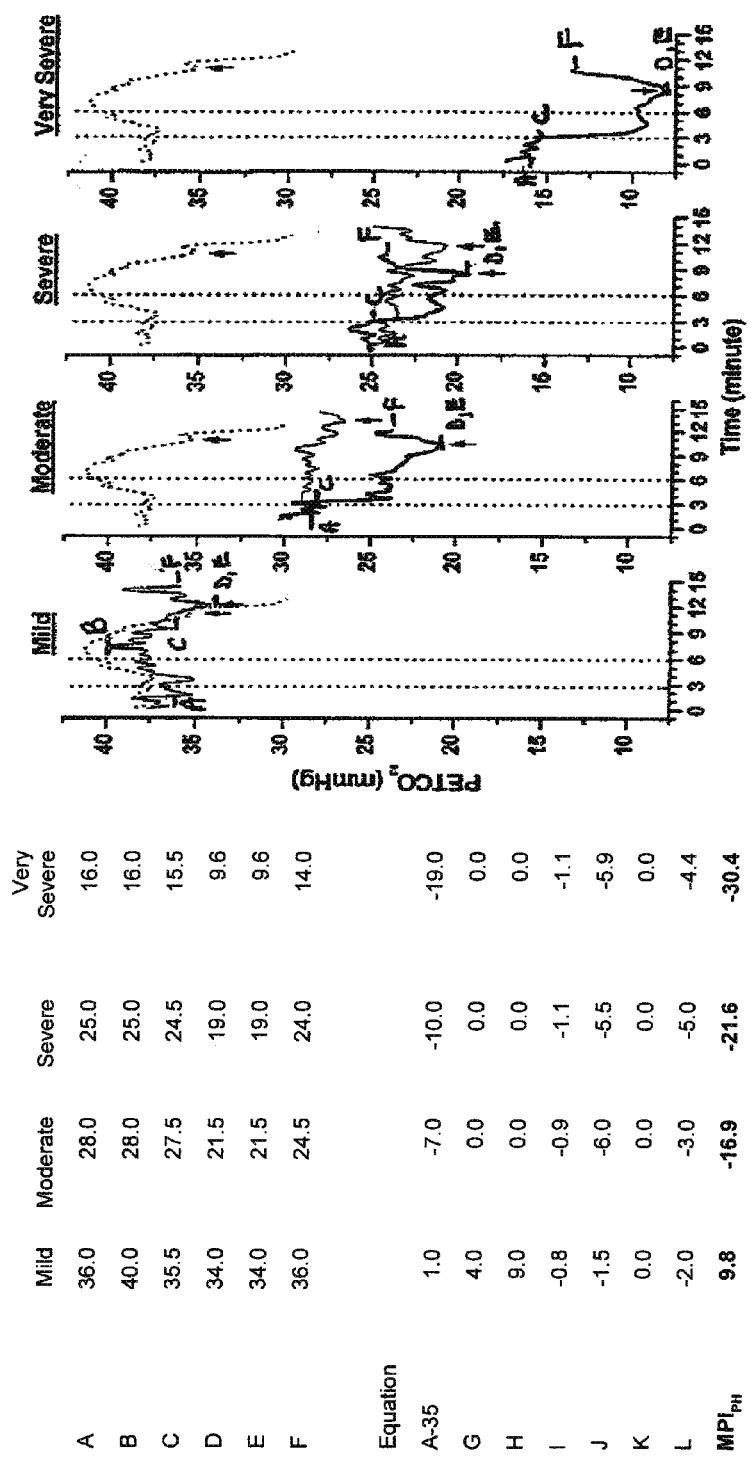
Figure 8 – Sample Calculations

Fig. 9 – Classification of Severity

| Class | Symptomatic Profile | $MPI_{PH}$ delta ETCO2 (rest to exercise) > 1.8, no reversal in ETCO2 during exercise, Area O/Area U > 1 |
|---|---|---|
| | Normal, no PAH | |
| Class I | Patients with pulmonary hypertension but without resulting limitation of physical activity. Ordinary physical activity does not cause dyspnea or fatigue, chest pain, or near syncope | >= -10.0 and |
| Class II | Patients with pulmonary hypertension resulting in slight limitation of physical activity. They are comfortable at rest. Ordinary physical activity causes undue dyspnea or fatigue, chest pain or near syncope | <= -10.0 and > -20.0 |
| Class III | Patients with pulmonary hypertension resulting in marked limitation of physical activity. They are comfortable at rest. Less than ordinary activity causes undue dyspnea or fatigue, chest pain, or near syncope | <= -20.0 and > -30 |
| Class IV | Patients with pulmonary hypertension with inability to carry out any physical activity without symptoms. These patients manifest signs of right heart failure. dyspnea and/or fatigue may even be present at rest. Discomfort is increased by any physical activity. | <= -30.0 |

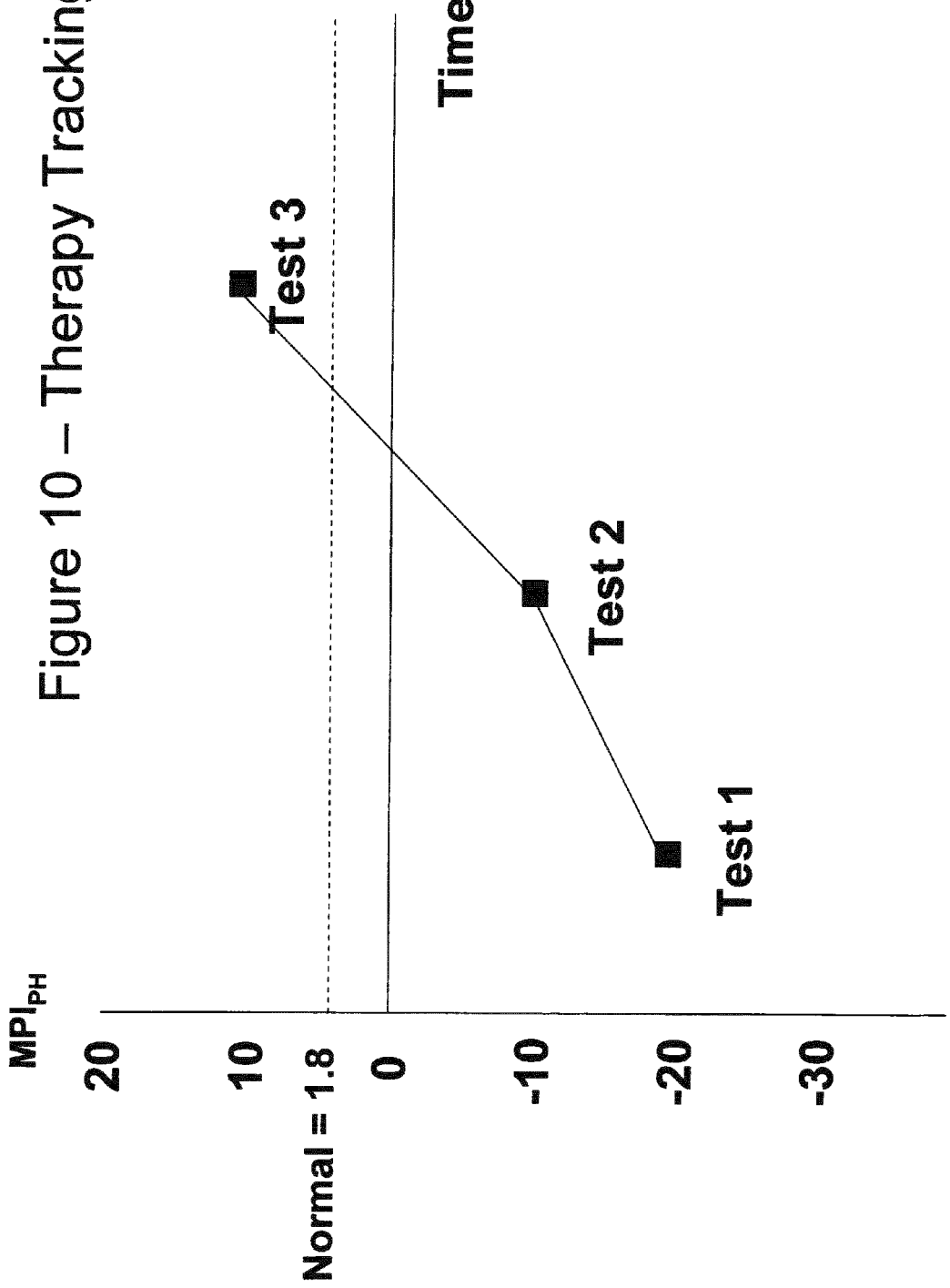

PATTERN RECOGNITION SYSTEM FOR CLASSIFYING THE FUNCTIONAL STATUS OF PATIENTS WITH PULMONARY HYPERTENSION, INCLUDING PULMONARY ARTERIAL AND PULMONARY VASCULAR HYPERTENSION

CROSS-REFERENCED TO RELATED APPLICATIONS

This application is a Continuation-In-Part of application Ser. No. 12/209,376, filed Sep. 12, 2008, which is a non-provisional application of Application No. 60/993,998, filed Sep. 17, 2007, and this application claims priority from those applications which are also deemed incorporated by reference in their entirety in this application.

STATEMENT REGARDING FEDERALLY SPONSORED RESEARCH OR DEVELOPMENT

Not applicable

BACKGROUND OF THE INVENTION

I. Field of the Invention

The present invention relates generally to the field, including pulmonary arterial and pulmonary vascular hypertension, of medical diagnosis and specifically to a process of identifying patients with Pulmonary Hypertension (PH), including pulmonary arterial and pulmonary vascular hypertension and classifying the functional status of these patients to assess the severity of the disease. The present method provides a more sensitive, physiologic, and easier to use method than currently available classification systems. In addition, the present invention provides feedback during long-term follow-up and treatment in patients with PH.

II. Related Art

The early symptoms of PH—such as Dyspnea, dizziness and fatigue—are often mild and are common to many other conditions. At rest there are often no symptoms and no apparent signs of illness. As a result, diagnosis can be delayed for months or even years meaning that PH is frequently not recognized until the disease is relatively advanced.[1] PH is often diagnosed only once other conditions have been investigated and ruled out.

The non-specific nature of symptoms associated with PH means that the diagnosis cannot be made on symptoms alone. A series of investigations is required to make an initial diagnosis, to refine that diagnosis in terms of clinical class of pulmonary hypertension, and to evaluate the degree of functional and hemodynamic impairment. Current PH evaluation and classification (type, functional capacity, hemodynamics) methods include blood tests and immunology, HIV test, abdominal ultrasound scan, 6-minute walk test (6-MWT), peak $VO_2$, right heart catheterization, and vaso-reactivity testing. It is with exercise that the sympathetic and neurohormonal systems trigger increased vasoconstriction of the pulmonary arteriolar vascular beds, thus causing an elevation in pulmonary vascular resistance and reduced blood flow through the pulmonary vascular circuit. The reduced blood flow is mismatched to the air flow in the bronchioles and alveoli.

It is often that the exercise state is not evaluated by any pulmonary function parameters that truly represent gas exchange in the lungs. Instead, walking distance and peak oxygen uptake are measured.

A well-known current classification system was formulated by the New York Heart Association (NYHA) and the World Health Organization (WHO). The NYHA system places patients in one of four categories based on how much they are limited during physical activity.

TABLE 1

NYHA/WHO Classification of Functional Status of Patients with Pulmonary Hypertension[1]

| Class | Symptomatic profile |
|---|---|
| Class I | Patients with pulmonary hypertension but without resulting limitation of physical activity. Ordinary physical activity does not cause Dyspnoea or fatigue, chest pain or near syncope |
| Class II | Patients with pulmonary hypertension resulting in slight limitation of physical activity. They are comfortable at rest Ordinary physical activity causes undue dyspnoea or fatigue, chest pain or near syncope |
| Class III | Patients with pulmonary hypertension resulting in marked limitation of physical activity. They are comfortable at rest. Less than ordinary activity causes undue dyspnoea or fatigue, chest pain or near syncope |
| Class IV | Patients with pulmonary hypertension with inability to carry out any physical activiry without symptoms. These patients manifest signs of right heart failure. Dyspnoea and/or fatigue may even be present at rest. Discomfort is increased by any physical activity. |

The major shortcoming of the NYHA/WHO system is that it relies on subjective observations by the patient and interpretation of those observations by the physician.

The 6-minute walk test, while simple and convenient, has many limitations including issues relating to reproducibility, sensitivity, and essentially a plateau in functional assessment when patients have less functional impairment.

The logistics of performing an exercise test to maximal exertion, including laboratory staffing, direct physician supervision and test duration, in addition to the increased level of patient discomfort, does not lend to conducting this procedure in a serial fashion over short time intervals (i.e. several weeks-months). In addition, it has been found that maximum exercise levels are not representative of lower level, activities of daily living.

SUMMARY OF THE INVENTION

The present advance, to a large extent, obviates the problems discussed in the foregoing for the NYHA/WHO Classification system, for peak $VO_2$ testing for functional classification, and for the 6-minute hall walk for therapy tracking. In accordance with the present invention, it has been found that a continuous, numeric multiparametric ranking score will provide a functional classification for PH patients that is easier to visualize and interpret. Moreover, this multiparametric score is obtained by either exercising the patient to a maximal value, or by utilization of gas exchange variables commonly measured during submaximal exercise indicative of everyday patient activity. The MPI provides multiparametric representation regarding PH that is clear and easy to understand.

The present invention involves the use of exercise-related data in a method of pattern recognition for diagnosing the presence of Pulmonary Hypertension and classifying the functional status of patients with chronic PH using a multiparametric index ($MPI_{PH}$).

The present invention provides a single multiparametric score that can be used to quantify the degree of severity of a patient with PH by combining certain Feature Extraction Steps, for example, steps 1-8, explained below, with an additional term, A–35 mmHg, as will be explained. In combination, the value for $MPI_{PH}$ may be expressed as follows:

$$MPI_{PH}=(A-35\text{ mmHg})+G*W1+H*W2+I*W3+J*W4+K*W5+L*W6$$

Where A-L are individual ranking parameters derived from exercise data and W1-W6 are weighting factors.

The values for A-L having been derived previously in Feature Extraction Steps 1-8 (see FIGS. 7,8, for example). One objective in formulating the value for $MPI_{PH}$ in the manner of the present invention is to obtain a negative value for patients with PH, and to obtain a value the magnitude of which is larger with increasing severity of the disease. This is also evident from the table in FIG. 8. Because the term "G" represents an appropriate directional change in $ETCO_2$ in response to exertion, although transient, this may be indicative of pulmonary venous hypertension, rather than pulmonary arterial hypertension. Therefore, it has been determined that a relatively larger value for G (first rise) is indicative of lower severity; thus, a positive value of G reduces the negative total $MPI_{PH}$. Because the term "H" represents an increase in pulmonary blood flow or improved matching of ventilation to perfusion, it has been determined that a relatively larger value for H (delay) is indicative of lower severity; thus, a positive value of H reduces the negative total $MPI_{PH}$ value. Similarly, it has been determined that the presence of a rebound K, during exercise, is also indicative of lower severity, thus a positive value of K also reduces the negative total $MPI_{PH}$ value.

The values for W1-W6 in the above equation are statistical weighting factors that may or may not equal 1 (a value of 1, of course will not alter the total value of $MPI_{PH}$). A value of 1 was used for all the weighting factors in conjunction with FIG. 7 and FIG. 8. By conducting clinical trials involving PH patients with known PH disease, confirmed by right heart catheterization, individual weighting factors can be determined to fine tune the computation of $MPI_{PH}$.

The data utilized in the present invention, cardiopulmonary exercise gas exchange measurements, is obtained 1) at rest, 2) during physical exercise testing performed in accordance with a standardized workload protocol as the forcing function to elicit physiologic changes resulting from the workload, and 3) during a short recovery period following exercise termination.

Physiologic changes are measured using a cardiopulmonary exercise testing system (CPX) to measure selected variables (parameters) associated with oxygen consumption, $VO_2$, carbon dioxide production, $VCO_2$, end tidal $CO_2$, $ETCO_2$, ventilation, VE, and heart rate, HR.

In accordance with a preferred method, a cardiopulmonary exercise gas exchange analysis is made for each test data set.

Whereas, the data gathering aspect involves known techniques and analysis, and the calculations for formulating predictive assessments are available in the scientific literature (see the bibliography in References), it is aspects of the feature extraction mechanism and the classification scheme from which the invention enables an observer to gain new and valuable insight into the present condition and condition trends in patients.

Importantly, it has been discovered that the change in end tidal $CO_2$ ($ETCO_2$) during and related to submaximal or peak exercise can be used as a key prognostic indicator in the evaluation of Pulmonary Hypertension.

This has been used as a basis for deriving a novel $MPI_{PH}$ score as described that offers a simplified, easier to interpret quantitative means for the diagnosis and the classification of the functional status of PH.

BRIEF DESCRIPTION OF THE DRAWINGS

In the drawings:

FIG. 4 illustrates a normal $ETCO_2$ response to exercise.

FIG. 5 illustrates the calculation of the areas over the resting $ETCO_2$ baseline during exercise (Area O) and the area under the resting $ETCO_2$ baseline during exercise (Area U);

FIG. 6 illustrates features extracted from the $ETCO_2$ vs. time plot;

FIG. 7 illustrates an analysis flow chart to compute $MPI_{PH}$;

FIG. 8 illustrates sample calculations from Yasunobu;

FIG. 9 illustrates a description scheme employed by the present invention for displaying the resultant $MPI_{PH}$ values with the NYHA/WHO Class juxtaposed onto the scale; and FIG. 10 illustrates a trend plot of test time-sequential $MPI_{PH}$ values.

DETAILED DESCRIPTION

Figure 1:
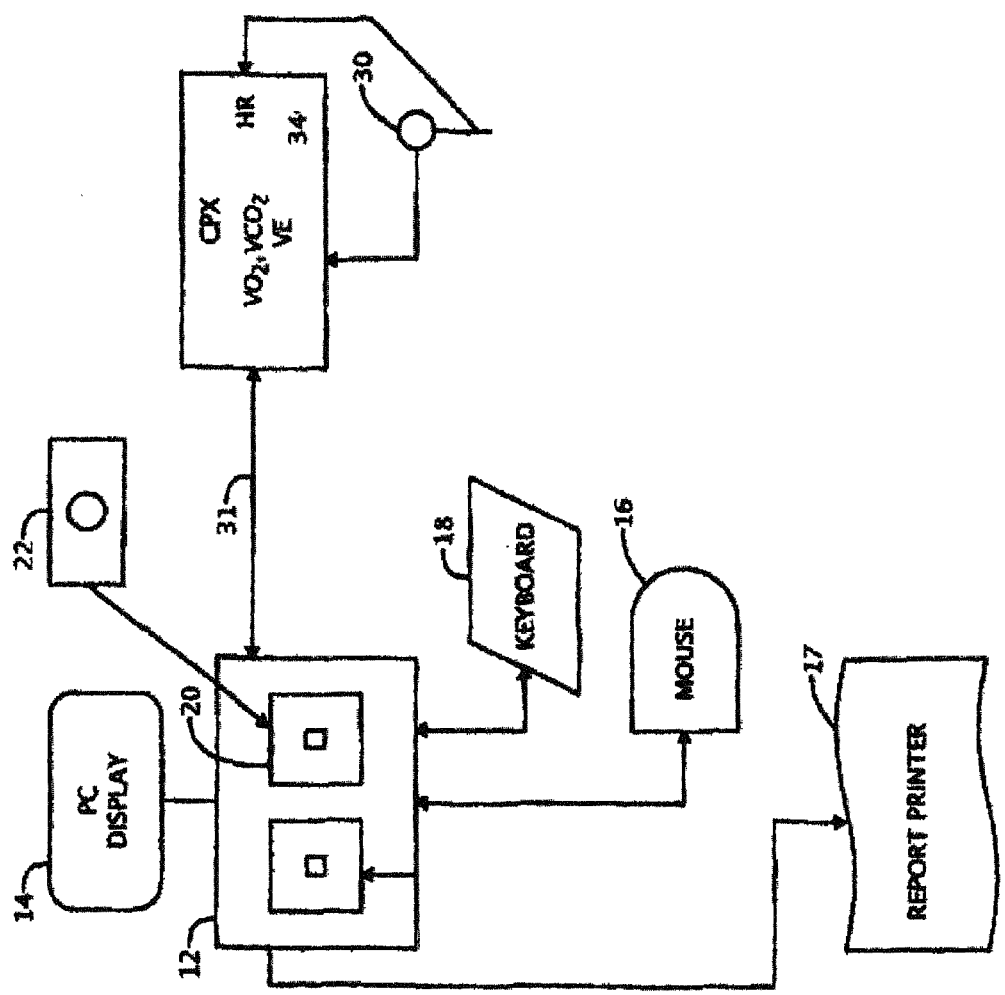
FIG. 1 is a schematic drawing that illustrates the functional components of a CPX testing system usable with the present invention.

The following detailed description, including the use of patient data, is intended to be exemplary of a preferred method of utilizing the concepts of the present invention and is not intended to be exhaustive or limiting in any manner with respect to similar methods and additional or other steps which might occur to those skilled in the art. The following description further utilizes illustrative examples, which are believed sufficient to convey an adequate understanding of the broader concepts to those skilled in the art, and exhaustive examples are believed unnecessary.

It is becoming increasingly clear in the literature that the change in $ETCO_2$ during submaximal exercise is a valuable prognostic indicator.[2]

"While both $VE/VCO_2$ and ($ETCO_2$) were significant univariate prognostic markers, the latter CPX variable appears to provide superior prognostic information during low-intensity exercise".

Another study[3] concluded that "Resting $ETCO_2$ appears to add prognostic value to variables that are well established and commonly collected in clinical practice. The fact that resting $PetCO_2$ is easily, cheaply, and noninvasively obtained portends high clinical promise for this measurement".

ADVANTAGES

Recently Yasanobu and colleagues[4] have demonstrated the detection of PH by functional evaluation using cardiopulmonary gas exchange measurements. They eloquently demonstrated that the real time monitoring of end-expired $CO_2$ was able to confirm the existence of PH when a reverse decrease in end tidal $ETCO_2$ occurred during mild to moderate exercise as assessed up to the anaerobic threshold (AT) with a typical rebound in $ETCO_2$ upon the cessation of exercise. Of interest was the high correlation between the decrease in $ETCO_2$ and mean Pulmonary Artery Pressure (PAP).

However, no method for a systematic, computerized analysis of the breath-by-breath $ETCO_2$ response curve during rest, exercise, and recovery is presented or suggested. Furthermore, how such data can be used to track therapy is not addressed.

Using the method described below in accordance with the invention, the $MPI_{PH}$ was computed for each of the four patient tests represented in the Yasunobu study. The feature extraction method performed on the $ETCO_2$ vs. time plot is depicted in FIG. 6. In reference to FIG. 6, measurements A through F represent the following physiologic phenomena. Resting $ETCO_2$ represents the matching of ventilation to pulmonary perfusion and typically will not disclose any type of significantly elevated PVR, until during an exercise stimulus. As PH worsens, an elevated Pulmonary Vascular Resistance (PVR) will exist even at rest. Measurement H represents the "delay time" in sympathetic and neurohormonal induced Measurements A and B, depending on the degree/severity of pulmonary vasoconstriction, represents the severity of PH. Measurement G represents a transient, normal response to exercise whereby the $ETCO_2$ begins to increase at the start of exercise. It is believed that this transient rise, then fall, of $ETCO_2$ is reflective of pulmonary venous, rather than pulmonary arterial, hypertension. The slope, measurement I, of the $ETCO_2$ drop following exercise onset reflects the rate of increased PVR. Measurement E represents the degree of mismatching and expiration of $CO_2$ (partial pressure) just at the end of exercise while measurement F reflects the degree of attenuation in PVR due to the sympathetic exercise stimulus being withdrawn. The potential increase in $ETCO_2$ at end exercise, as compared to the lowest $ETCO_2$ value at point "D" or the nadir, represents an increase in pulmonary blood flow or improved matching of ventilation to perfusion.

General Considerations—The present invention includes a pattern recognition system consisting of a) a cardiopulmonary exercise gas exchange analyzer that gathers the observations to be classified or described, b) a feature extraction mechanism that computes numeric information from the observations, and c) a classification or description scheme that does the actual job of classifying or describing observations based on the extracted features.

Data Gathering: As indicated and shown in FIG. 2, the general class of data utilized in the present invention, cardiopulmonary exercise gas exchange measurements, is obtained 1) at rest, 2) during physical exercise testing performed in accordance with a standardized workload protocol as the forcing function to elicit physiologic changes resulting from the workload, and 3) during a short recovery period following exercise termination. The data measured during exercise quantifies how an individual is able to function in the physical world in terms of the physiologic changes that the individual experiences when engaged in the performance of daily physical work.

The physiologic changes are measured using a cardiopulmonary exercise testing system (CPX) to measure selected variables associated with oxygen consumption, $VO_2$, carbon dioxide production, $VCO_2$, end tidal $CO_2$, $ETCO_2$, ventilation, VE, and heart rate, HR.

As indicated, the data gathering aspect of the invention involves known techniques and analyses, and the calculations for formulating predictive assessments are readily available in the scientific literature (see the bibliography in References). However, by means of aspects of the feature extraction mechanism and the classification scheme, the present invention enables an observer to gain new and valuable insight into the present condition and condition trends in patients. Thus, in accordance with a preferred method, a cardiopulmonary exercise gas exchange analysis is made for each test data set. The performance of such a test is well understood by individuals skilled in the art, and no further explanation of this is believed necessary.

Equipment—With this in mind typical hardware is shown in FIG. 1, which illustrates typical equipment whereby a cardiopulmonary exercise test (CPX) may be conducted and the results displayed in accordance with the method of the present invention. The system is seen to include a data processing device, here shown as a personal computer of PC 12, which comprises a video display terminal 14 with associated mouse 16, report printer 17 and a keyboard 18. The system further has a floppy disc handler 20 with associated floppy disc 22. As is well known in the art, the floppy-disc handler 20 input/output interfaces comprise read/write devices for reading prerecorded information stored, deleting, adding or changing recorded information, on a machine-readable medium, i.e., a floppy disc, and for providing signals which can be considered as data or operands to be manipulated in accordance with a software program loaded into the RAM or ROM memory (not shown) included in the computing module 12.

The equipment used in the exercise protocol can be a simple stair step of a known height. A CPX testing system 34 interfaces with the subject 30 during operation of the exercise test. The physiological variables may be selected from heart rate (HR), ventilation (VE), rate of oxygen uptake or consumption ($VO_2$) and carbon dioxide production ($VCO_2$) end tidal $CO_2$ ($ETCO_2$) or other variables derived from these basic measurements. Physiological data collected is fed into the computing module 12 via a conductor 31, or other communication device.

Figure 2:
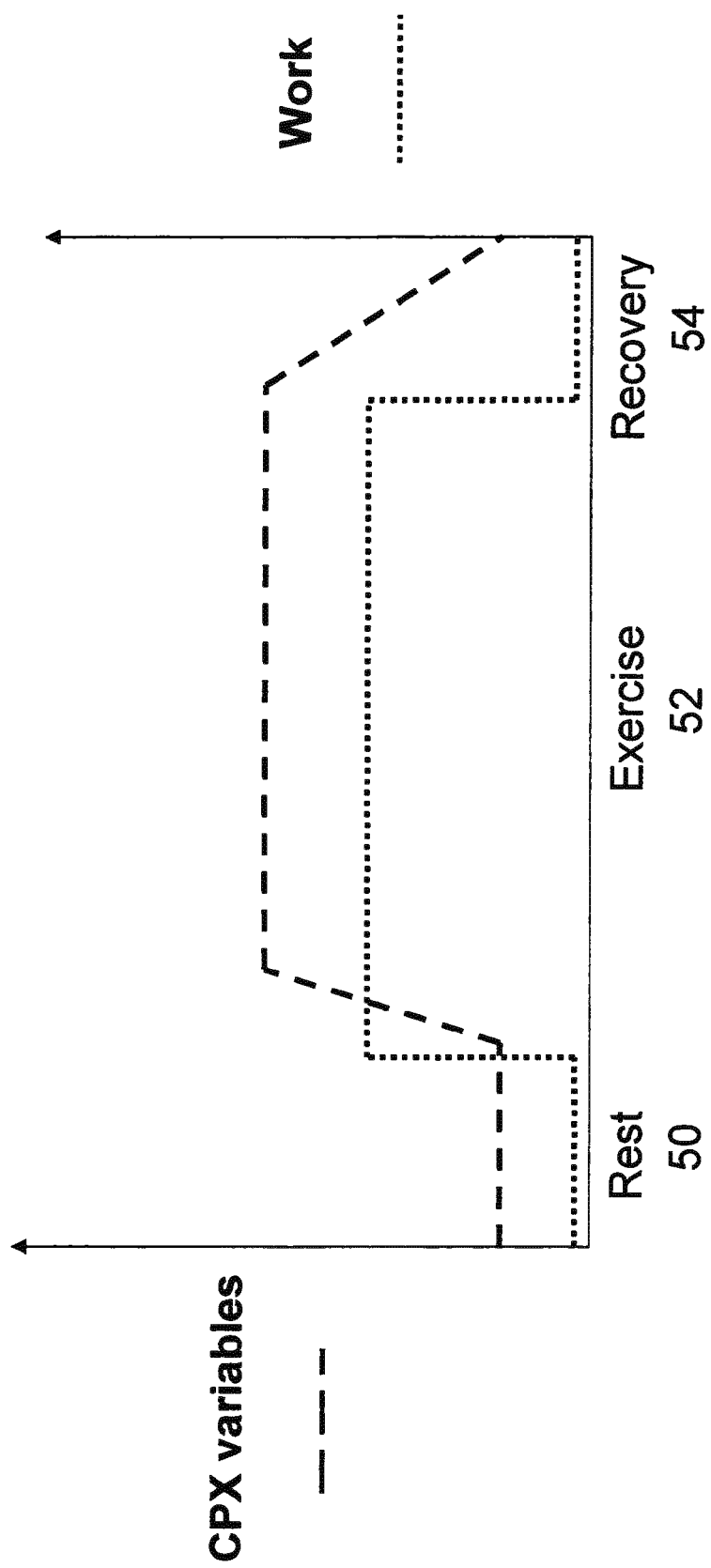
FIG. 2 is a schematic drawing that illustrates one form of exercise protocol that is used to place a volume load on the cardiopulmonary system.

The workload protocol is illustrated in FIG. 2 and is organized in to a rest phase 50, and exercise phase 52, and a recovery phase 54. Although not required, the workload may also be quantified by requiring the patient to maintain a desired stepping cadence by the addition of an audible metronome that guides the frequency of the steps taken during the exercise phase.

Figure 3:
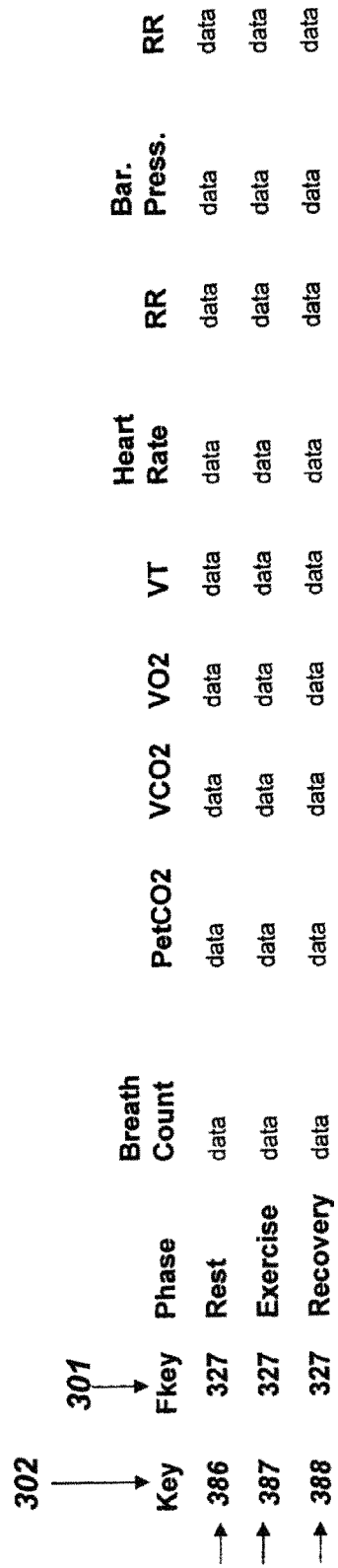
FIG. 3 illustrates an organization of the measured data once it is acquired from the cardiopulmonary exercise gas exchange analyzer.

All data acquired by the CPX system is stored in a relational database as illustrated in FIG. 3. Most importantly, data for each patient and each test is stored into separate subsets of data representing the rest phase 386, the exercise phase 387, and the recovery phase 388 for use by the feature extraction mechanism.

Feature Extraction Steps

Step 1—Detection—An impetus for the use of statistical pattern recognition comes from new methods of analyzing cardiopulmonary data published in the scientific literature over the past five years. From the bibliography in References (2), statistical values for the normal value and cutoff point for the difference between the last 30 second average value of $ETCO_2$ or $PetCO_2$ pressure in mmHg during rest (point A in FIG. 6) and the last 30 second average of $ETCO_2$ (mmHg) during exercise (point E in FIG. 6) can be obtained. If the difference in these two values is greater than or equal to 1.8 (mmHg, the patient exhibits no increased risk of death and no presence of PH; thus, the remaining analysis is not and need not be performed. As a further test of whether any given patient test exhibits PH, two areas are computed: 1) Area O (see FIGS. 5 and 6) is the area over the resting $ETCO_2$ baseline bounded by the measured $ETCO_2$ waveform during the exercise phase or period; 2) Area U (see FIGS. 5 and 6) is the area under the resting $ETCO_2$ baseline bounded by the measured $ETCO_2$ waveform during the exercise phase. If the ratio of Area O/Area U is greater than 1, the patient exhibits no presence of PH; thus, the remaining analysis is not and need not be performed. In accordance with the present method, the following steps 2-8 are used to determine the severity of PH in others, and, with respect to steps 2-8, reference is also made to FIG. 6.

Step 2—Delay time—The delay time (H) is calculated by first determining inflection point C, the first $ETCO_2$ value during exercise that is less than A. The delay time is calculated by subtracting the time value for C from the starting time of the exercise phase.

Step 3—First rise—The first rise, measurement G, is calculated by subtracting the average resting value of $ETCO_2$ (A) from inflection point B, the maximum $ETCO_2$ value greater than A and which occurs prior to reaching inflection point C.

Step 4—Nadir—The smallest value of $ETCO_2$ occurring after point C is then determined as inflection point D.

Step 5—Slope—The next step is to compute the regression line through those data points for $ETCO_2$ from inflection point C to D. The general form for the regression equation is $$y = a + bx$$

The constant a is the intercept, b is the slope. The a and b values are chosen so that the sum of squared deviations from the line is minimized. The best line is called the regression line, and the equation describing it is called the regression equation.

In FIG. 6, an example illustrates the measured data for the cardiopulmonary data pairs with the plot of the dashed regression line and the slope value I.

Step 6—Drop—The next step is to compute the maximum drop in $ETCO_2$, J, by subtracting the inflection point D from inflection point C.

Step 7—Intra-exercise rebound—The next step is to compute the value of the intra-exercise rebound. This step may yield a value of 0 in the case where $ETCO_2$ continues to drop until the end of the exercise phase. The value of K is computed by subtracting inflection point D from E.

Step 8—Recovery rebound—The final step is to compute the value of the recovery rebound L by subtracting the value of the last $ETCO_2$ data point during recovery, F, from E.

Description Scheme $MPI_{PH}$ Score

In FIG. 8, 4 patient tests representing different degrees of severity are presented. As can be seen, the patterns are similar to that illustrated in FIG. 6. However, the values for A, as derived in Step 1 above, are shifted downward from the normal value for $ETCO_2$ at rest (estimated to be 35 mmHg based on previous studies to date). In order to provide a single, multiparametric score that can be used to quantify the degree of severity of a patient with PH, the present invention combines the Feature Extraction Steps 1-8 with an additional term, A−35 mmHg. In combination, the value for $MPI_{PH}$ is then expressed as $$MPI_{PH} = (A - 35\ mmHg) + G*W1 + H*W2 + I*W3 + J*W4 + K*W5 + L*W6$$

The values for A-L have been described previously in Feature Extraction, Steps 1-8. The basic objective in formulating the value for $MPI_{PH}$ in this way is to obtain a negative value for patients with PH, and to obtain a value the magnitude of which is larger with increasing severity of the disease. As indicated above, because the term G represents an appropriate directional change in $ETCO_2$ in response to exertion, although transient, it has been determined that the presence of first rise G is indicative of lower severity, thus a positive value of G reduces the negative total $MPI_{PH}$ value. Similarly, because the term H represents an increase in pulmonary blood flow or improved matching of ventilation to perfusion, it has been determined that a relatively larger value for H (delay) is indicative of lower severity, thus a positive value of G reduces the negative total $MPI_{PH}$ value. Similarly, it has been determined that the presence of an intra-exercise rebound K is also indicative of lower severity, thus a positive value of K reduces the negative total $MPI_{PH}$ value.

A flowchart for computing $MPI_{PH}$ is depicted in FIG. 7 in which the $MPI_{PH}$ score is computed for FIG. 6. Using this same flowchart, the $MPI_{PH}$ values for FIG. 8 are computed and displayed on the left side of FIG. 8.

The values for W1-W6 in the above equation are weighting factors that may or may not equal 1 (a value of 1 not altering the total value of $MPI_{PH}$). As indicated by conducting clinical trials involving PH patients with known PH disease, pulmonary vascular or pulmonary arterial, and confirmed by right heart catheterization, individual weighting factors can be determined to fine tune the computation of $MPI_{PH}$ for determining severity and type.

Description Scheme $MPI_{PH}$ Based Classification System

In order to introduce the objectively measured value of $MPI_{PH}$ into the more familiar NYHA/WHO classification system, the two are juxtaposed as illustrated in FIG. 9. The addition of the top line for an objective, non-invasive determination of the presence of PH extends the classification system to include a diagnostic indicator for the disease itself. When combined with other cardiopulmonary exercise test variables, such as ventilatory efficiency ($VE/VCO_2$ slope and ratio) and change in oxygen saturation ($SpO_2$), the present invention provides further diagnostic information to confirm or rule out the presence of PH.

Description Scheme

Trend Plot

In order to provide a rapid assessment of the effect of any given therapy for PH over time, one example of a trend plot for $MPI_{PH}$ values over time is illustrated in the graph in FIG. 10. In this example, the individual values of $MPI_{PH}$ for each test date are plotted serially. However, there is no limitation intended in terms of the type of graph utilized or the visual effects employed. Alternatively, the Area O/Area U ratio can be plotted similarly in a time-sequential manner.

When combined with other submaximal cardiopulmonary exercise variables ($VE/VCO_2$ slope, oxygen saturation ($SPO_2$)) that have been demonstrated to change with drug therapy[5], trend plotting of all will allow physicians to manage PH treatment for their patients.

The invention has been described in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as the equipment details and operating procedures can be accomplished without departing from the scope of the invention itself.

REFERENCES

1. Primary Pulmonary Hypertension. Lancet 1998; 352: 719-25-Gaine S P, Rubin L J
2. Ventilatory Expired Gas at Low-Intensity Exercise Predicts Adverse Events and Is Related To Neurohormonal Markers in Patients with Heart Failure, Ross Arena, PhD, PT, Dean MacCarter, PhD, Thomas P. Olson PhD, Sophie Lalande PhD, Maile L. Ceridon PhD, Lyle J. Olson, MD and Bruce Johnson, PhD *J Card Fail* 2009 August; 15(6):482-8. Epub 2009 Feb. 10
3. The partial pressure of resting end-tidal carbon dioxide predicts major cardiac events in patients with systolic heart failure, Ross Arena, PhD, PT, Jonathan Myers, PdD, Mary Ann Peberdy, MD, Daniel Bensimhon, MD, Paul Chase, Med, and Marco Guazzi, MD, PhD Am Heart J 2008; 156:982-88
4. End-tidal PCO2 Abnormality and Exercise Limitation in Patients with Primary Pulmonary Hypertension. Yuji Yasunobu, et al. Chest 2005; 127:1637-1646
5. Ventilatory Efficiency and Dyspnea on Exertion Improvements are Related to Reduced Pulmonary Pressure in Heart Failure Patients Receiving Sildenafil, *Int J Cardiol.* 2009 Mar. 27. [Epub ahead of print] PMID: 19329196, Guazzi M, Myers J, Peberdy M A, Bensimhon D, Chase P, Arena R

What is claimed is:

1. A method of pattern recognition for diagnosing the presence of chronic pulmonary hypertension (PH) and evaluating patients with that condition, comprising:
   (a) classifying the functional status of patients with a chronic condition by conducting a course of evaluation using a system for providing a pattern that characterizes said functional status using a calculated multiparametric set of data that reflects the status of a patient ((multiparametric index ($MPI_{PH}$));
   (b) obtaining a plurality of measurements, including a plurality of weighted individual Ranking Parameters (RP), from a patient, said measurements being taken a plurality of times during the course of evaluation wherein said evaluation includes using a cardiopulmonary exercise gas exchange analyzer to perform sub-maximal cardiopulmonary exercise testing bouts;
   (c) using a computing device to process data obtained in said plurality of measurements each time said measurements are taken to determine a plurality of weighted RPs by multiplying each by a selected weighting factor to obtain the $MPI_{PH}$ and obtain a statistical pattern of $MPI_{PH}$ values based on said measurements being taken a plurality of times to thereby determine the ongoing functional status of said patient;
   (d) wherein said $MPI_{PH}$ is based on the sum of a plurality of said individual RPs combined with weighing factors (W) and wherein said plurality of RPs are selected at least in part from end tidal $CO_2$ ($ET CO_2$) cardiopulmonary exercise test related measurements;
   (e) classifying said functional status based on the $MPI_{PH}$; and
   (f) wherein calculated statistical values consider a normal value (NV) and cutoff point (COP);
   (g) wherein said cardiopulmonary exercise bouts, comprise:
   performing a gas exchange test on a patient, wherein the gas exchange test includes a rest phase, an exercise phase, and a recovery period, wherein the patient performs submaximal or maximal exercise during the exercise phase;
   obtaining a plurality of physiological measurements, including end tidal $CO_2$ on a breath-by-breath basis during the gas exchange test;
   determining a first value associated with an average end tidal $CO_2$ value during at least a portion of the rest phase;
   determining a second value associated with a rise at the beginning of the exercise phase;
   determining a third value associated with the first end tidal CO2 value that is less than the first value;
   determining a fourth value associated with nadir of the exercise PetCO2;
   determining a fifth value that is associated with the last 30 seconds of exercise;
   determining a sixth value that is associated with the last end tidal CO2 value of recovery;
   determining a seventh value that is determined by subtracting the second value from the first value
   determining an eighth value that is obtained by subtracting the time at which the first value occurred from the time at which the third value occurred;
   determining a ninth value that is associated with the maximum drop in end tidal CO2 obtained by computing the slope of the line of regression from the third value to the fourth value and a tenth value that is associated with a maximum drop in end tidal $CO_2$ obtained by subtracting the fourth value from the third value;
   determining an eleventh value that is obtained by subtracting the fourth value from the fifth value;
   determining a twelfth value that is obtained by subtracting the sixth value from the fifth value;
   calculating a score associated with a weighted combination of at least the first value, the seventh value, the eighth value, the ninth value, the tenth value, the eleventh value, and the twelfth value; and
   determining a functional status of the patient based on the score and one or more of the 12 measurements described above, wherein the functional status is associated with a degree of severity of functional and hemodynamic impairment of the patient.

2. A method as in claim 1 wherein the cardiopulmonary exercise test measurements are gathered from exercise that includes peak exercise bouts.

3. A method as in claim 1 wherein cardiopulmonary exercise test measurements are displayed during low intensity or peak exercise and stored as data sets, each set being associated with a rest phase, an exercise phase, and a recovery phase.

4. A method as in claim 1 wherein the measured $MPI_{PH}$ is located and displayed in a time sequential manner on a numeric axis that ranges from positive to negative values.

5. A method as in claim 1 wherein the measured $MPI_{PH}$ juxtaposed on the NYHA/WHO Classification of Functional Status of Patients with Pulmonary Hypertension.

6. A method as in claim 1 wherein the measured $MPI_{PH}$ is used to determine whether the patient exhibits either pulmonary arterial hypertension or pulmonary venous hypertension.

7. A method as in claim 1 further comprising repeating the calculation of $MPI_{PH}$ at spaced intervals for therapy tracking.

8. A method as in claim 7 wherein the $MPI_{PH}$ is used to determine whether the patient exhibits either pulmonary arterial hypertension or pulmonary venous hypertension.

9. A method as in claim 1 further comprising using the calculated $MPI_{PH}$ to diagnose the severity of a pulmonary hypertension condition.

10. A method of pattern recognition for diagnosing the presence of chronic pulmonary hypertension (PH) and evaluating patients with that condition, comprising:
  (a) classifying the functional status of patients with a chronic condition by conducting a course of evaluation using a system for providing a pattern that characterizes said functional status using a calculated multiparametric set of data that reflects the status of a patient ((multiparametric index ($MPI_{PH}$));
  (b) obtaining a plurality of measurements, including a plurality of weighted individual Ranking Parameters (RP), from a patient, said measurements being taken a plurality of times during the course of evaluation wherein said evaluation includes using a cardiopulmonary exercise gas exchange analyzer to perform sub-maximal cardiopulmonary exercise testing bouts;
  (c) using a computing device to process data obtained in said plurality of measurements each time said measurements are taken to determine a plurality of weighted RPs by multiplying each by a selected weighting factor to obtain the $MPI_{PH}$ and obtain a statistical pattern of $MPI_{PH}$ values based on said measurements being taken a plurality of times to thereby determine the ongoing functional status of said patient;
  (d) wherein said $MPI_{PH}$ is based on the sum of a plurality of said individual RPs combined with weighing factors (W) and wherein said plurality of RPs are selected at least in part from end tidal $CO_2$ ($ET\ CO_2$) cardiopulmonary exercise test related measurements;
  (e) classifying said functional status based on the $MPI_{PH}$; and
  (f) wherein calculated statistical values consider a normal value (NV) and cutoff point (COP);
  (g) wherein said cardiopulmonary exercise bouts, comprise:
    performing a gas exchange test on a patient, wherein the gas exchange test includes a rest phase, an exercise phase, and a recovery period, wherein the patient performs submaximal or maximal exercise during the exercise phase;
    obtaining a plurality of physiological measurements, including end tidal $CO_2$ on a breath-by-breath basis during the gas exchange test;
    determining a first value associated with an average end tidal $CO_2$ value during at least a portion of the rest phase;
    determining a second value associated with a rise at the beginning of the exercise phase;
    determining a third value associated with the first end tidal CO2 value that is less than the first value;
    determining a fourth value associated with nadir of the exercise PetCO2;
    determining a fifth value that is associated with the last 30 seconds of exercise;
    determining a sixth value that is associated with the last end tidal CO2 value of recovery;
    determining a seventh value that is determined by subtracting the second value from the first value
    determining an eighth value that is obtained by subtracting the time at which the first value occurred from the time at which the third value occurred;
    determining a ninth value that is associated with the maximum drop in end tidal CO2 obtained by computing the slope of the line of regression from the third value to the fourth value and a tenth value that is associated with a maximum drop in end tidal $CO_2$ obtained by subtracting the fourth value from the third value;
    determining an eleventh value that is obtained by subtracting the fourth value from the fifth value;
    determining a twelfth value that is obtained by subtracting the sixth value from the fifth value;
    calculating a score associated with a weighted combination of at least the first value, the seventh value, the eighth value, the ninth value, the tenth value, the eleventh value, and the twelfth value; and
    determining a functional status of the patient based on the score and one or more of the 12 measurements described above, wherein the functional status is associated with a degree of severity of functional and hemodynamic impairment of the patient;
  (h) wherein the $MPI_{PH}$ is computed using the equation $$MPI_{PH}=(A-35\ mmHg)+G*W1+H*W2+I*W3+J*W4+K*W5+L*W6$$

Where A and G-L are individual Ranking Parameters and W1-W6 are weighting factors for the particular Ranking Parameters, the weighting factors being determined by either retrospective statistical analysis or by statistical analysis of breath-by-breath cardiopulmonary exercise test data acquired from patients with diagnosed presence of pulmonary hypertension (PH) prospectively over time.

11. A method as in claim 10 wherein the cardiopulmonary exercise test measurements are gathered from exercise that includes peak exercise bouts.

12. A method as in claim 10 wherein cardiopulmonary exercise test measurements are displayed during low intensity or peak exercise and stored as data sets, each set being associated with a rest phase, an exercise phase, and a recovery phase.

13. A method as in claim 10 wherein one or more Ranking Parameters A and G-L are determined, in part, by a feature extraction mechanism that computes, as the measured value, the difference between the average value of select variables or ratios of select variables obtained as data at rest, during exercise and during recovery.

14. A method as in claim 10 wherein:
  (a) A=the last 30 second average $ETCO_2$ value during rest;
  (b) G=the initial, transient rise in $ETCO_2$ after the start of exercise;
  (c) H=the delay time between A and the first $ETCO_2$ value during exercise less than A;
  (d) I is determined, in part, by a feature extraction mechanism that computes, as the measured value, the slope of the line of regression obtained from select data pairs obtained during sub-maximal exercise;
  (e) J represents the maximum drop in $ETCO_2$ during submaximal exercise;
  (f) K represents intra-exercise rebound during submaximal exercise;
  (g) L represents recovery rebound (one minute); and
  (h) the value for one or more weighting factors W1-W6 is calculated, in part, from statistical values in the scientific literature or from breath-by-breath cardiopulmonary exercise test data acquired from patients with diagnosed presence of PH prospectively over time.

15. A method as in claim 14 wherein selected measurements are used to determine whether the patient exhibits either pulmonary arterial hypertension or pulmonary venous hypertension.

* * * * *